(12) United States Patent
Jacobson et al.

(10) Patent No.: US 10,240,194 B2
(45) Date of Patent: Mar. 26, 2019

(54) METHODS FOR NUCLEOTIDE SEQUENCING AND HIGH FIDELITY POLYNUCLEOTIDE SYNTHESIS

(75) Inventors: Joseph Jacobson, Newton, MA (US); Daniel Schindler, Newton, MA (US)

(73) Assignee: Gen9, Inc., Cambridge, MA (US)

( * ) Notice: Subject to any disclaimer, the term of this patent is extended or adjusted under 35 U.S.C. 154(b) by 0 days.

(21) Appl. No.: 13/697,182

(22) PCT Filed: May 13, 2011

(86) PCT No.: PCT/US2011/036433
§ 371 (c)(1),
(2), (4) Date: May 28, 2013

(87) PCT Pub. No.: WO2011/143556
PCT Pub. Date: Nov. 17, 2011

(65) Prior Publication Data
US 2013/0244884 A1    Sep. 19, 2013

Related U.S. Application Data

(60) Provisional application No. 61/334,426, filed on May 13, 2010, provisional application No. 61/347,207, filed on May 21, 2010, provisional application No. 61/363,066, filed on Jul. 9, 2010.

(51) Int. Cl.
*C12Q 1/6874* (2018.01)
(52) U.S. Cl.
CPC .................. *C12Q 1/6874* (2013.01)
(58) Field of Classification Search
CPC ................. C12Q 1/6874; C12Q 1/68
USPC .......................................................... 506/2
See application file for complete search history.

(56) References Cited

U.S. PATENT DOCUMENTS

| | | |
|---|---|---|
| 5,143,854 A | 9/1992 | Pirrung et al. |
| 5,288,514 A | 2/1994 | Ellman |
| 5,384,621 A | 1/1995 | Winkler et al. |
| 5,510,270 A | 4/1996 | Fodor et al. |
| 5,527,681 A | 6/1996 | Holmes |
| 5,541,061 A | 7/1996 | Fodor et al. |
| 5,599,675 A | 2/1997 | Brenner |
| 5,639,603 A | 6/1997 | Dower et al. |
| 5,700,637 A | 12/1997 | Southern |
| 5,700,642 A | 12/1997 | Monforte et al. |
| 5,739,386 A | 4/1998 | Holmes |
| 5,770,358 A | 6/1998 | Dower et al. |
| 5,830,655 A | 11/1998 | Monforte et al. |
| 6,375,903 B1 | 4/2002 | Cerrina et al. |
| 6,401,267 B1 | 6/2002 | Radoje Drmanac |
| 6,800,439 B1 | 10/2004 | McGall et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 7,276,338 B2 | 10/2007 | Jacobson |
| 7,604,941 B2 * | 10/2009 | Jacobson .................. B82Y 5/00 435/6.14 |
| 2002/0081582 A1 | 6/2002 | Gao et al. |
| 2003/0013101 A1 | 1/2003 | Balasubramanian |
| 2003/0065633 A1 | 4/2003 | Belshaw et al. |
| 2003/0186226 A1 | 10/2003 | Brennan et al. |
| 2004/0106728 A1 | 6/2004 | McGall et al. |
| 2005/0112608 A1 * | 5/2005 | Grossman et al. ................ 435/6 |
| 2006/0008833 A1 | 1/2006 | Jacobson |
| 2006/0240443 A1 | 10/2006 | Lodes |
| 2007/0219367 A1 | 9/2007 | Schepinov et al. |
| 2009/0263802 A1 * | 10/2009 | Drmanac .............. C12Q 1/6874 435/6.12 |
| 2010/0063264 A1 | 3/2010 | Jacobson |
| 2010/0105052 A1 | 4/2010 | Drmanac et al. |
| 2010/0138162 A1 | 6/2010 | Kain et al. |

FOREIGN PATENT DOCUMENTS

| | | |
|---|---|---|
| WO | WO 98/031831 | 7/1998 |
| WO | WO 99/042813 | 8/1999 |
| WO | WO 02/004597 | 1/2002 |
| WO | WO 0210443 A1 * | 2/2002 |
| WO | WO 03/040410 | 5/2003 |
| WO | WO 03/046223 | 6/2003 |
| WO | WO 03/064026 | 8/2003 |
| WO | WO 03/064027 | 8/2003 |
| WO | WO 03/064699 | 8/2003 |
| WO | WO 03/065038 | 8/2003 |
| WO | WO 03/066212 | 8/2003 |
| WO | WO 03/100012 | 12/2003 |
| WO | WO 04/029586 | 4/2004 |
| WO | WO 04/031351 | 4/2004 |
| WO | WO 04/031399 | 4/2004 |
| WO | WO 06/002281 | 1/2006 |
| WO | WO 07/133831 | 11/2007 |

(Continued)

OTHER PUBLICATIONS

Mir et al., Sequencing by Cyclic Ligation and Cleavage (CycLiC) Directly on a Microarray Captured Template, Nucleic Acids Research, 2009, 37(1), 1-8.*
Bethell et al., "From Monolayers to Nanostructured Materials: An Organic Chemist's View of Self-Assembly,"J. Electroanal Chem. 409: 137 (1996).
Blanchard, Alan. "Synthetic DNA Arrays," Genetic Engineering. Plenum Press. 20: 111-123 (1998).
Broude et al., "Enhanced DNA sequencing by hybridization," Proc Natl Acad Sci U S A.. 91(8):3072-30766.

(Continued)

*Primary Examiner* — Amy M Bunker
(74) *Attorney, Agent, or Firm* — Choate, Hall & Stewart LLP; Brenda Herschbach Jarrell; Robert N. Sahr

(57) ABSTRACT

Methods of obtaining sequence information about target polynucleotide having a predefined sequence are disclosed. The methods include sequencing by ligation and sequencing by polymerase.

23 Claims, 12 Drawing Sheets

Specification includes a Sequence Listing.

(56) References Cited

FOREIGN PATENT DOCUMENTS

| WO | WO 2010025310 A2 | * | 3/2010 |
|---|---|---|---|
| WO | WO-2011/143556 A1 | | 11/2011 |

OTHER PUBLICATIONS

Colvin et al., "Semiconductor Nanocrystals Covalently Bound to Metal Surfaces with Self-Assembled Monolayers," J. Am. Chem. Soc. 114: 5221-5230 (1992).
Deng et al., "Oligonucleotide ligation assay-based DNA chip for multiplex detection of single nucleotide polymorphism," Biosens Bioelectron. 19(10):1277-1283 (2004).
Drmanac et al., "Sequencing by Hybridization (SBH): Advantages, Achievements, and Opportunities," Advances in Biochemical Engineering, Biotechnology. 77: 75-010 (2002).
Dubiley et al., "Fractionation, phosphorylation and ligation on oligonucleotide microchips to enhance sequencing by hybridization," Nucleic Acids Res. 25(12):2259-2265 (1997).
Duggan et al., "Expression Profiling Using cDNA Microarrays," Nat. Genet. 21:10-14 (1999).
Fan et al., "Parallel genotyping of human SNPs using generic high-density oligonucleotide tag arrays," Genome Research. 10(6):853-860 (2000).
Grabar et al., "Preparation and Characterization of Au Colloid Monolayers," Analyt. Chem. 67:73-743 (1995).
Gunderson et al., "Mutation detection by ligation to complete n-mer DNA arrays," Genome Res. 8(11):1142-53 (1998).
Harvey et al., "Enzymatic breakage and joining of deoxyribonucleic acid. IX. Synthesis and properties of the deoxyribonucleic acid adenylate in the phage T4 ligase reaction," J. Biol. Chem. 246(14):4523-4530 (1971).
Housby et al., "Fidelity of DNA ligation: a novel experimental approach based on the polymerisation of libraries of oligonucleotides," Nucleic Acids Res. 26(18):4259-4266 (1998).
Lee et al., "Fabricating RNA microarrays with RNA-DNA surface ligation chemistry," Anal Chem. 77(23):7832-7837 (2005).
McGall et al., "Light-Directed Synthesis of High-Density Oligonucleotide Arrays Using Semiconductor Photoresists," Pro. Natl. Acad. Sci. 93(24):13555-13560 (1996).
Mikhailovich et al., "Identification of rifampin-resistant *Mycobacterium tuberculosis* strains by hybridization, PCR, and ligase detection reaction on oligonucleotide microchips," Journal of Clinical Microbiology. 39(7):2531-2540 (2001).
Mir et al., "Sequencing by Cyclic Ligation and Cleavage (CycLiC) Directly n a Microarray Captured Template," Nucleic Acids Research. 37(1): E5-1 (2009).
Pon et al., "Hydroquinone-O,O'-diacetic acid ('Q-linker') as a replacement for succinyl and oxalyl linker arms in solid phase oligonucleotide synthesis," Methods Mol. Biol. 20:465-496 (1993).
Shumaker et al., "Mutation detection by solid phase primer extension," Human Mutation. 7(4):346-354 (1996).
Stekel et al., "Microarrays: Making Them and Using Them," Microarray Bioinformatics. Cambridge University Press. 1-18 (2003).
Syvänen, A.C., "Accessing Genetic Variation: Genotyping Single Nucleotide Polymorphisms," Nature Reviews Genetics. 2(12): 930-942 (2001).
Verma et al., "Modified Oligonucleotides: Synthesis and Strategy for Users," Annu. Rev. Biochem. 6:99-134 (1998).
International Search Report issued in International Application No. PCT/US2011/03433 dated Oct. 18, 2011.
International Search Report for PCT/US11/36433 (Methods for Nucleotide Sequencing and High Fidelity Polynucleotide Synthesis, filed May 13, 2011) issued by ISA/EPO, 4 pages (Oct. 18, 2011).
Margulies, M. et al., Genome Sequencing in Open Microfabricated High Density Picoliter Reactors, Nature, 437(7057): 376-380 (2005).
Seo, T.S. et al., Four-color DNA sequencing by synthesis on a chip using photocleavable fluorescent nucleotides, PNAS, 102(17): 5926-5931 (2005).
Shendure, J. et al., Accurate Multiplex Polony Sequencing of an Evolved Bacterial Genome, Science, 309: 1729-1732 (2005).
Written Opinion for PCT/US11/36433 (Methods for Nucleotide Sequencing and High Fidelity Polynucleotide Synthesis, filed May 13, 2011) issued by ISA/EPO, 7 pages (Oct. 18, 2011).

* cited by examiner

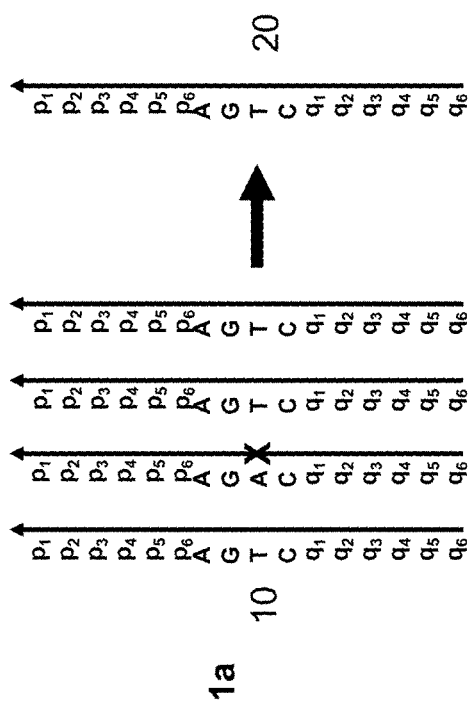
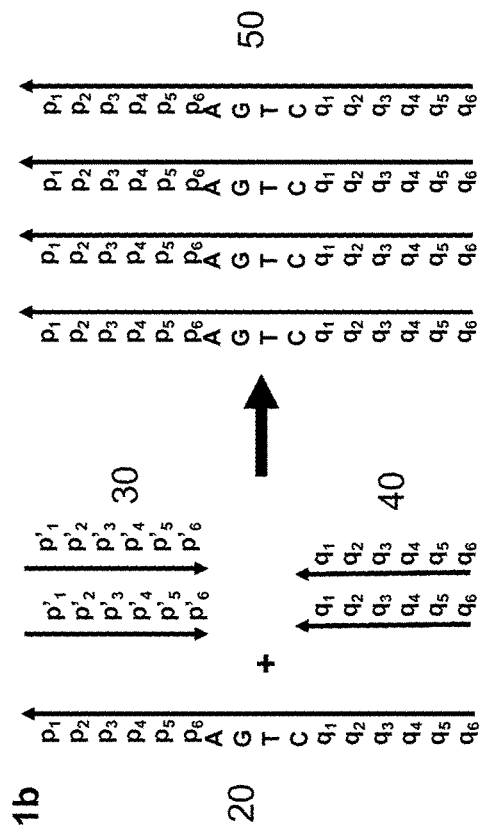
Figure 1
Figure 1a
Figure 1b

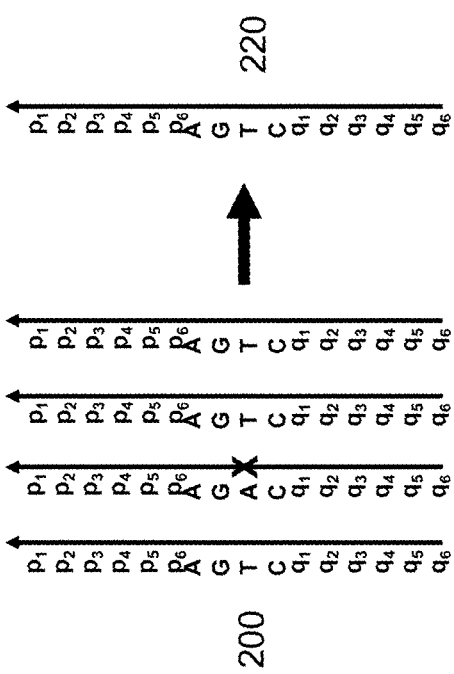
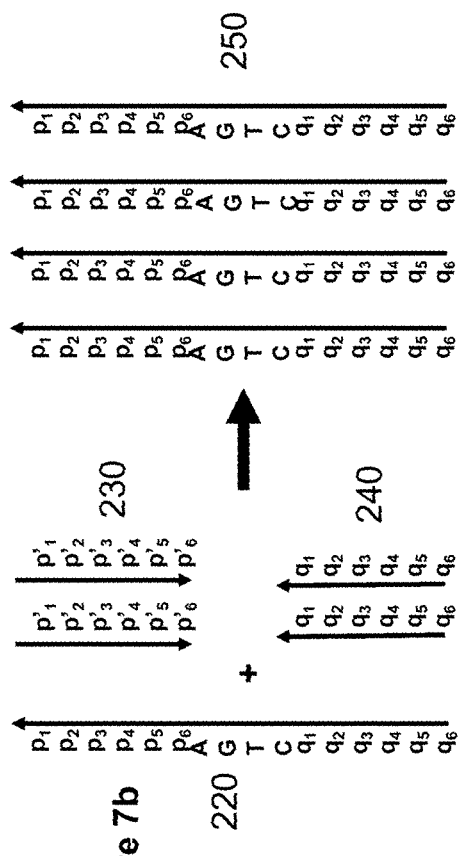
Figure 7
Figure 7a
Figure 7b

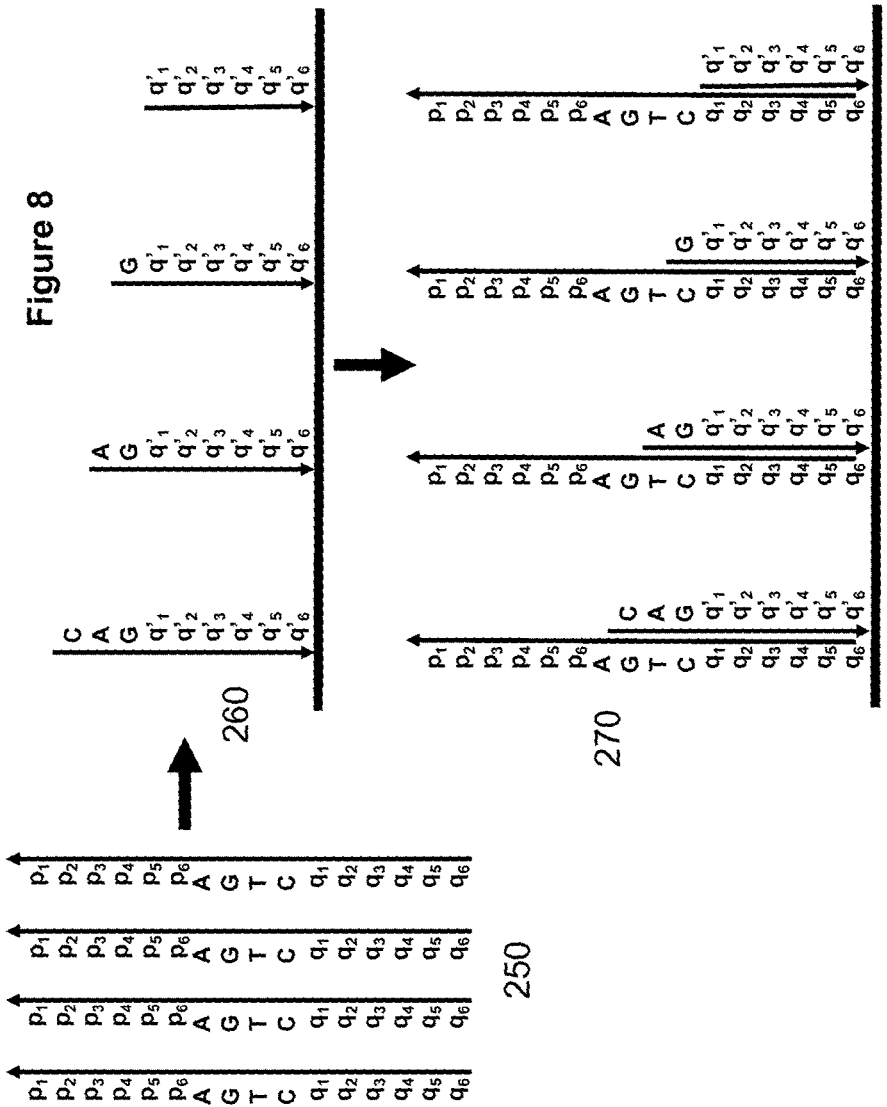

290

METHODS FOR NUCLEOTIDE SEQUENCING AND HIGH FIDELITY POLYNUCLEOTIDE SYNTHESIS

RELATED APPLICATIONS

This application is a National Phase application of International Application No. PCT/US2011/36433, filed May 13, 2011, which claims priority to and the benefit of U.S. Provisional Patent Application Ser. No. 61/334,426, filed May 13, 2010; U.S. Provisional Patent Application Ser. No. 61/347,207, filed May 21, 2010; and U.S. Provisional Patent Application Ser. No. 61/363,066, filed Jul. 9, 2010, the contents of each of the foregoing applications are incorporated herein by reference in their entirety.

STATEMENT REGARDING FEDERALLY SPONSORED RESEARCH

This invention was made with United States Government support under the cooperative agreement number 70NANB7H7034N awarded by the National Institute of Standards and Technology. The United States Government has certain rights in the invention.

FIELD OF THE INVENTION

Methods and devices provided herein generally relate to sequencing polynucleotides. More particularly, methods and devices provided herein generally relate to sequencing polynucleotides of predefined sequence. The invention relates generally to synthesis of long polynucleotide sequences.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., polynucleotide sequences longer than about 400 base pairs. Furthermore, the error rate of chemically-synthesized oligonucleotides (deletions at a rate of 1 in 100 bases and mismatches and insertions at about 1 in 400 bases) exceeds the error rate obtainable through enzymatic means of replicating an existing nucleic acid (e.g., PCR). There is therefore a need for fast, and low cost re-sequencing of methods.

SUMMARY

Aspects of the invention relates to methods and compositions for sequencing target polynucleotides having a predefined sequence. According to some aspects, the present invention permits highly parallel sequencing of target nucleic acids. In preferred embodiment, the target nucleic acids have a predefined sequence and are synthesized de novo. According to one embodiment, the method for identifying a target polynucleotide having a predefined sequence, comprises (a) providing a support comprising a plurality of anchor oligonucleotides, wherein each plurality anchor oligonucleotide comprises a predefined sequence complementary to the predefined sequence of the target polynucleotide and is immobilized to a discrete feature of the support; (b) hybridizing the target polynucleotide sequence to the plurality of anchor oligonucleotides; (c) contacting the target polynucleotide to at least one sequencing oligonucleotide probe, wherein each oligonucleotide probe comprises a unique nucleotide at a first interrogation position and a label; (d) ligating the sequencing oligonucleotide probe to the anchor oligonucleotide; and (e) detecting the hybridization of the sequencing oligonucleotide probe to the target polynucleotide thereby identifying the target polynucleotide having the predefined sequence. Steps c), d) and e) may be repeated to identify a second nucleotide at a second interrogation position. Preferably, the support comprises a plurality of discrete features and wherein each plurality of anchor oligonucleotide is immobilized on a distinct discrete feature. In some embodiments, the sequencing oligonucleotide comprises at least three degenerate bases and/or the sequencing oligonucleotide comprises at least three degenerate bases and a unique interrogating nucleotide sequence. In some embodiments, the nucleotide interrogation position is at the sequencing oligonucleotide 3' terminus or at the 5' terminus. In preferred embodiments, the label comprises a fluorescence tag. In some embodiments, the plurality of anchor oligonucleotides has a different length and differs from each other from at least one additional predefined base. In some embodiments, anchor oligonucleotide comprises at least there degenerate bases and differs from each other from at least one additional predefined nucleotide. In some embodiments, the target polynucleotide comprises a first primer binding site at its 5' end and a second primer binding site at its 3' end. The target polynucleotide may be first amplified before being hybridized to the plurality of anchor oligonucleotides. In some embodiments, the target polynucleotide is contacted with four sequencing oligonucleotide probes, each oligonucleotide probe comprising a unique nucleotide at a first interrogation position and a different label.

According to one embodiment, the method provides a method for identifying a target polynucleotide having a predefined sequence, the method comprising (a) providing a support comprising a plurality of anchor oligonucleotides, wherein each plurality of oligonucleotides comprises a predefined sequence complementary to the predefined sequence of the target polynucleotide and is immobilized to a discrete feature of the support; (b) hybridizing the target polynucleotide sequence to the plurality of anchor oligonucleotides; (c) contacting the hybrid target polynucleotide-anchor oligonucleotide with at least one labeled nucleotide; (d) extending the anchor oligonucleotide in a template dependent manner in presence of a polymerase; and (e) detecting the incorporation of the labeled nucleotide into the hybrid. Steps c), d) and e) may be repeated. In some embodiments, the hybrid target polynucleotide-anchor oligonucleotide is contacted with four different labeled nucleotides and each nucleotide is differently labeled. In some embodiments, each plurality of anchor oligonucleotides has a different length and differs from each other from at least one additional predefined base. In some embodiments, each anchor oligonucleotide comprises at least there degenerate bases and differs from each other from at least one additional predefined nucleotide. In some embodiments, the target polynucleotide comprises a first primer binding site at its 5' end and a second primer binding site at its 3' end. In some embodiments, the target polynucleotide is first amplified before being hybridized to the plurality of anchor oligonucleotides.

According to some embodiments, the method for identifying a target polynucleotide having a predefined sequence comprises (a) providing a support comprising a plurality of anchor oligonucleotides, wherein each plurality of anchor oligonucleotides comprises terminal region having a predefined sequence complementary to a predetermined region of a target polynucleotide having a predefined sequence; (b) contacting the anchor oligonucleotides with the target polynucleotide under conditions suitable to hybridize the predetermined region of the target polynucleotide to the terminal region of the anchor oligonucleotides; (c) contacting the target polynucleotide with at least one sequencing oligonucleotide probe, wherein each oligonucleotide probe comprises at least one interrogating nucleotide at a first interrogation position and a label; (d) ligating the sequencing oligonucleotide probe to the anchor oligonucleotide; and (e) detecting the hybridization of the sequencing oligonucleotide probe to the target polynucleotide thereby identifying the target polynucleotide having the predefined sequence. Optionally steps c) d) and e) are repeated to identify at least one nucleotide at a second interrogation position. In some embodiments, the different interrogation positions are consecutive. Yet in other embodiments, the different interrogation positions are not consecutive. The different interrogation positions may be separated by 2, 3, 4, 5, 6, or 7 nucleotides. In some embodiments, each sequencing probe comprises at its 3' end a different nucleotide sequence. The support preferably comprises a plurality of discrete features wherein each plurality of different anchor oligonucleotides is immobilized at a distinct discrete feature. In preferred embodiments, each plurality of anchor probe has a different sequence and different length. Each plurality of anchor oligonucleotides has a different length and may differ from each other from at least one additional predefined interrogation nucleotide. The sequencing oligonucleotides can comprise at least three degenerate bases and a unique interrogating nucleotide sequence, or at least three degenerate bases and two or more interrogating nucleotide sequences. Preferably, the nucleotide interrogation position is at the sequencing oligonucleotide 3' terminus. In some embodiments, the label comprises a fluorescence tag.

The target polynucleotide can comprise a first primer binding site at its 5' end and a second primer binding site at its 3' end and can be first amplified before being hybridized to the plurality of anchor oligonucleotides. In some embodiments, after hybridization to the anchor oligonucleotides, the target polynucleotide is contacted with four sequencing oligonucleotide probes, wherein each oligonucleotide probe comprises a unique nucleotide at a first interrogation position and a different label. In some embodiments, sixteen different sequencing probes comprising two interrogation positions can be used wherein each of the sixteen sequencing probe is differently labeled. The sequencing oligonucleotides are ligated and the ligating step can be performed using Tth DNA ligase under condition promoting selective ligation. In some embodiments, the method further comprising the step of removing unligated probe after the step of ligating.

According to some embodiments, the method for identifying a target polynucleotide having a predefined sequence comprises (a) providing a support comprising a plurality of anchor oligonucleotides, wherein each plurality of anchor oligonucleotides comprises a terminal region having a predefined sequence complementary to a predetermined region of a target polynucleotide having a predefined sequence; (b) contacting the anchor oligonucleotides with the target polynucleotide under conditions suitable to hybridize the predetermined region of the target polynucleotide to the terminal region of the anchor oligonucleotides; (c) contacting the target polynucleotide with a plurality of sequencing oligonucleotide probes, wherein each plurality of oligonucleotide probes comprises an interrogating RNA nucleotide at an interrogation position and a label; (d) ligating the plurality of sequencing oligonucleotide probes to the plurality of anchor oligonucleotides; (e) detecting the presence or absence of the label wherein the presence of label is correlated to a polynucleotide sequence having the predefined sequence; (f) cleaving the plurality of sequencing oligonucleotide 3' to the RNA base; and (g) repeating steps c) through f) if the presence of the label is detected until the target polynucleotide having predefined sequence is identified. In some embodiments, the RNA base is adjacent to the 3' end nucleotide of the plurality of sequencing oligonucleotides and the plurality of sequencing oligonucleotide are cleaved 3' to the RNA base such as the anchor oligonucleotides are extended by a single nucleotide. Yet in other embodiments, the RNA base is two bases upstream of the 3' end nucleotide of the plurality of sequencing oligonucleotides, and the plurality of sequencing oligonucleotide are cleaved 3' to the RNA base such as the anchor oligonucleotides are extended by a dinucleotide.

According to some embodiments, the method for identifying a target polynucleotide having a predefined sequence comprises (a) providing a support comprising a plurality of anchor oligonucleotides, wherein each plurality of anchor oligonucleotides comprises a terminal region having a predefined sequence complementary to a predetermined region of a target polynucleotide having a predefined sequence; (b) contacting the anchor oligonucleotides with the target polynucleotide under conditions suitable to hybridize the predetermined region of the target polynucleotide to the terminal region of the anchor oligonucleotides; (c) contacting the target polynucleotide with a plurality of sequencing oligonucleotide probes, wherein each plurality of oligonucleotide probes comprises a single RNA nucleotide at the 3' end of the plurality of sequencing oligonucleotide probes and a label; (d) ligating the plurality of sequencing oligonucleotide probes to the plurality of anchor oligonucleotides; (e) detecting the absence of the label wherein the absence of label is correlated to a polynucleotide sequence not having the predefined sequence; and (f) cleaving the plurality of sequencing oligonucleotide 3' to the RNA base, thereby regenerating the support comprising the plurality of anchor oligonucleotides.

According to some embodiments, the method for identifying a target polynucleotide having a predefined sequence (a) providing a support comprising a plurality of anchor oligonucleotides, wherein each plurality of anchor oligonucleotides comprises a terminal region having a predefined sequence complementary to a predetermined region of a target polynucleotide having a predefined sequence; (b) contacting the anchor oligonucleotides with the target polynucleotide under conditions suitable to hybridize the predetermined region of the target polynucleotide to the terminal region of the anchor oligonucleotides thereby forming at least one target polynucleotide-anchor oligonucleotide duplex; (c) contacting the at least one target polynucleotide-anchor oligonucleotide duplex with at least one labeled nucleotide; (d) extending the anchor oligonucleotide in a template dependent manner in presence of a polymerase; and (e) detecting the incorporation of the labeled nucleotide into the at least one target polynucleotide-anchor oligonucleotide duplex. Optionally repeating steps c), d) and e) are repeated. In some embodiments, the target polynucleotide-anchor oligonucleotide duplex is contacted with four different labeled nucleotides and wherein each nucleotide is differently labeled. Each plurality of anchor oligonucleotides has a different length and can differ from each other from at least one additional predefined nucleotide. In some embodiments, each plurality of anchor oligonucleotides comprises at least three degenerate bases and differs from each other from at least one additional predefined nucleotide. In some embodiments, the target polynucleotide comprises a first primer binding site at its 5' end and a second primer binding site at its 3' end. In some embodiments, the target polynucleotide is first amplified before being hybridized to the plurality of anchor oligonucleotides. In some embodiments, the support comprises a plurality of discrete features and wherein each plurality of anchor oligonucleotide is immobilized on a distinct discrete feature.

Aspects of the invention relate to a support for sequencing a target polynucleotide having a predefined sequence, the support comprising a plurality of oligonucleotides, wherein each plurality of oligonucleotides is immobilized at a distinct feature of the support, wherein each plurality of oligonucleotides has a different length and comprises a sequence having a terminal region having a predefined sequence, the predefined sequence being complementary to a predetermined region of a target polynucleotide.

BRIEF DESCRIPTION OF THE DRAWINGS

FIG. 1 is a schematic illustration of an embodiment of a method of preparation of a clonal ensemble of polynucleotide constructs with primer binding sites for use in the ligation based re-sequencing method.

FIGS. 7a and 7b are schematic illustration of an embodiment of a method of ligation-based re-sequencing oligonucleotide array using a sequencing probe having a ribonucleotide.

FIG. 8. is a schematic illustration of an embodiment of a method of ligation-based re-sequencing oligonucleotide array using a sequencing probe having a ribonucleotide.

DETAILED DESCRIPTION OF THE INVENTION

Figure 2:
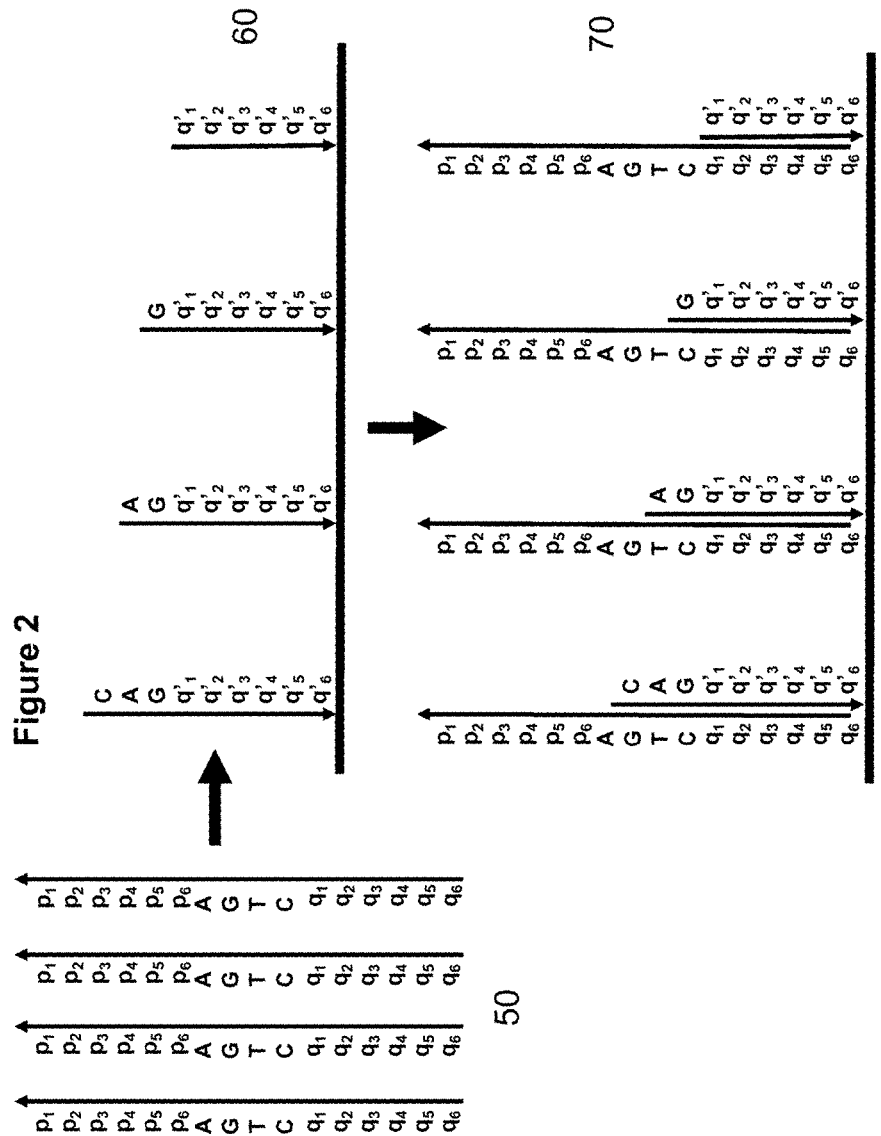
FIG. 2 is a schematic illustration of an embodiment of a method of ligation based re-sequencing oligonucleotide array.

Currently, there is much interest in the fabrication of synthetic DNA constructs such as oligonucleotides, genes, metabolic pathways and even parts of or entire genomes for various applications within conventional biology and medicine as well as synthetic biology. In typical practice oligonucleotides up to about 500 bases may be synthesized using a protection group chemical protocol. Longer constructs such as genes and longer length DNA constructs from about 100 bases to $10^5$ bases may be prepared by assembling smaller chemically synthesized oligonucleotides using processes such as the polymerase-based chain assembly (PCA) or ligation-based assembly methods. In each of these cases, the synthetic yield is not perfect and there is a probability of error in the final construct in which typical chemical synthesis error rates are on the order 0.5% to 2% and enzymatic assembly error rates may be on the order of 1 part in $10^5$. A number of error filtration and correction techniques such as error protein binding and cleavage preparations have been developed in order to further reduce error which comes from the chemical and/or enzymatic error rates. Nonetheless, in many cases it is desirable to confirm that the final construct is error free. Currently, this is typically accomplished by conventional or next generation primary sequencing. Unfortunately, these processes which are aimed at being able to determine a completely unknown sequence are unnecessarily time and cost consuming since in the present case one only wishes to determine whether a given construct is exactly the sequence which one intended or not (i.e. predetermined or pre-defined sequence). If the sequence does contain an error, one need not ascertain what the error is, rather, the very fact that the sequence of the construct contains an error is sufficient information to discard that construct and try (or sequence) another one. Here, we describe a process for ultrafast, ultralow cost (re-)sequencing of DNA constructs using oligonucleotide arrays.

Methods and devices for sequencing oligonucleotides as well long polynucleotides having a predefined sequence are provided herein. Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention are described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predefined sequence" or "predetermined sequence" are used interchangeably and means that the sequence of the polymer is known and chosen before synthesis or assembly of the polymer. In particular, aspects of the invention is described herein primarily with regard to the preparation of nucleic acids molecules, the sequence of the oligonucleotide(s) or polynucleotide(s) being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotides constructs to be synthesized. In one embodiment, "oligonucleotides" are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein.

In some embodiments, the target polynucleotide may be assembled using an assembly procedure and may include several parallel and/or sequential reaction steps in which a plurality of different nucleic acids or oligonucleotides are synthesized or immobilized, amplified, and are combined in order to be assembled (e.g., by extension or ligation as described herein) to generate a longer nucleic acid product to be used for further assembly, cloning, or other applications (see U.S. provisional application 61/235,677 and PCT application PCT/US09/55267 which are incorporate herein by reference in their entirety).

Some embodiments of the device and methods provided herein use oligonucleotides that are immobilized on a surface or substrate. As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticle and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein the term "array" refers to an arrangement of discrete features for storing, routing, amplifying, assembling and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support.

Arrays may be constructed, custom ordered or purchased from a commercial vendor (e.g., Agilent, Affymetrix, Nimblegen). Oligonucleotides are attached, spotted, immobilized, surface-bound, supported or synthesized on the discrete features of the surface or array as described above. Oligonucleotides may be covalently attached to the surface or deposited on the surface. Various methods of construction are well known in the art e.g. maskless array synthesizers, light directed methods utilizing masks, flow channel methods, spotting methods etc.

In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead-based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In yet another embodiment, a plurality of oligonucleotides may be attached or synthesized on nanoparticles. Nanoparticles includes but are not limited to metal (e.g., gold, silver, copper and platinum), semiconductor (e.g., CdSe, CdS, and CdS coated with ZnS) and magnetic (e.g., ferromagnetite) colloidal materials. Methods to attach oligonucleotides to the nanoparticles are known in the art. In another embodiment, nanoparticles are attached to the substrate. Nanoparticles with or without immobilized oligonucleotides can be attached to substrates as described in, e.g., Grabar et al., Analyt. Chem., 67, 73-743 (1995); Bethell et al., J. Electroanal. Chem., 409, 137 (1996); Bar et al., Langmuir, 12, 1172 (1996); Colvin et al., J. Am. Chem. Soc., 114, 5221 (1992). Naked nanoparticles may be first attached to the substrate and oligonucleotides can be attached to the immobilized nanoparticles.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824, 866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g. ink jet). In some embodiments, oligonucleotides are spotted on a support using, for example, a mechanical wave actuated dispenser.

One skilled in the art will appreciate that DNA microarrays can have very high density of oligonucleotides on the surface (approximately $10^8$ molecules per feature), which can generate steric hindrance to polymerases needed for PCR or to the ligase for ligation reactions. Theoretically, the oligonucleotides are generally spaced apart by about 2 nm to about 6 nm. For polymerases, a typical 6-subunit enzyme can have a diameter of about 12 nm. Therefore the support may need to be custom treated to address the surface density issue such that the spacing of surface-attached oligonucleotides can accommodate the physical dimension of the enzyme. For example, a subset of the oligonucleotides can be chemically or enzymatically cleaved, or physically removed from the microarray. Other methods can also be used to modify the oligonucleotides such that when primers are applied and annealed to the oligonucleotides, at least some 3' hydroxyl groups of the primers (start of DNA synthesis) are accessible by polymerase. The number of accessible 3' hydroxyl groups per spot can be stochastic or fixed. For example, the primers, once annealed, can be treated to remove some active 3' hydroxyl groups, leaving a stochastic number of 3' hydroxyl groups that can be subject to chain extension reactions. In another example, a large linker molecule (e.g., a concatamer) can be used such that one and only one start of synthesis is available per spot, or in a subset of the oligonucleotides per spot.

Aspects of the invention relate to support comprising a plurality of features wherein each different feature comprises a plurality of oligonucleotides designed to capture a predefined target to be sequenced. In some embodiments, the support comprises a plurality of features wherein each discrete feature comprises a different anchor oligonucleotide having a sequence complementary to the predefined target polynucleotide. Preferably, the anchor oligonucleotide or capture oligonucleotide is a single-stranded oligonucleotide. In some embodiments, the anchor oligonucleotide is an oligonucleotide designed to be complementary to at least a portion of the target polynucleotide (i.e. the anchor oligonucleotides comprises complementary bases). The anchor oligonucleotide may consist of at least 5, at least 6, at least 7, at least 10, at least 20, at least 30, at least 40 nucleotides. As illustrated in FIG. 2, the anchor oligonucleotide 60 comprises a sequence complementary to a portion of the target polynucleotide 50. In a preferred embodiment, each plurality of anchor oligonucleotides has a predefined sequence. In some embodiments, the anchor oligonucleotides sequence is complementary to the target polynucleotide. However, in other embodiments, the anchor oligonucleotides comprise degenerate sequences or universal bases. For example, the anchor oligonucleotides may comprise 2, 3 or more degenerated bases. Yet in other example, the anchor oligonucleotide comprises 2, 3 or more degenerated bases, and/or universal bases and one or more complementary base (complementary to the target polynucleotide). In preferred embodiments, each plurality of oligonucleotides has a common n-mer core and at least one additional nucleotide at the 5' or the 3' terminus which is complementary to the target polynucleotide. The plurality of anchor oligonucleotides differ in length by, for example, one nucleotide as depicted in FIG. 2 and FIG. 8. Yet in other embodiments, the plurality of anchor oligonucleotides differ in length by more than one nucleotide. In some embodiments, the anchor oligonucleotides differ by one consecutive complementary base. Yet in other embodiments, the anchor oligonucleotides may differ by the totality of its complementary sequence. Consequently, each plurality of anchor oligonucleotide has a length, sequence and a different terminal base. In some embodiments, the different terminal base allows the anchor oligonucleotide to be ligated to different sequencing oligonucleotide probes. In other embodiment, the different terminal base allows the anchor oligonucleotide to be extended by polymerase based reaction using different labeled base.

In some embodiments, pluralities of different single-stranded anchor oligonucleotides are immobilized at different features of a solid support. In some embodiments the oligonucleotides may be attached through their 5' end. In a preferred embodiment, the oligonucleotides are attached through their 3' end. It should be appreciated that by 3' end, it is meant the sequence downstream to the 5' end, and by 5' end it is meant the sequence upstream to the 3' end. For example, an oligonucleotide may be immobilized on the support via a nucleotide sequence (e.g., a degenerate binding sequence), linker or spacer (e.g., a moiety that is not involved in hybridization). In some embodiments, the anchor oligonucleotide comprises a spacer or linker to separate the sequence complementary to the target polynucleotide from the support. Useful spacers or linkers include photocleavable linkers, or other traditional chemical linkers. In one embodiment, oligonucleotides may be attached to a solid support through a cleavable linkage moiety. For example, the solid support may be functionalized to provide cleavable linkers for covalent attachment to the oligonucleotides. The linker moiety may be of six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., Annu Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. The cleavable moiety may be removed under conditions which do not degrade the oligonucleotides. Preferably the linker may be cleaved using two approaches, either (a) simultaneously under the same conditions as the deprotection step or (b) subsequently utilizing a different condition or reagent for linker cleavage after the completion of the deprotection step.

Sequencing by Ligation

In some aspect of the invention, the target polynucleotide is sequenced by sequencing by ligation methods. Sequencing by ligation methods typically employs the use of degenerate oligonucleotides and protein ligase to discriminate among target polynucleotides having one or more mismatch. Sequencing by ligation relies upon the sensitivity of DNA ligase for base-pairing mismatches i.e. on the fidelity of the DNA ligase to only join probes that are perfectly complementary to the target polynucleotide to which they hybridized. Moreover, sequencing by ligation relies on the ability of DNA ligases to discriminate mispaired bases downstream and upstream of the ligation junction, one or more mismatch in the ligation junction inhibiting the ligation reaction.

In some embodiments, the methods of sequencing by ligation use a combination of anchor probes immobilized on a solid support and sequencing probes. In a first step, the target polynucleotide is hybridized to the plurality of anchor oligonucleotides immobilized on discrete features. The resulting hybrid comprising the hybridized target polynucleotide is then exposed to sequencing oligonucleotide probes having different labels. Preferably, the sequencing probes comprising four different nucleotides at the terminal end are differently labeled. In some embodiments, the target polynucleotide is exposed to four sequencing oligonucleotide probes with different labels. As used herein "sequencing probes" refers to oligonucleotides designed to provide the identity of one or more nucleotide at a particular detection position of a target polynucleotide. Sequencing probes hybridize preferably to regions with the target polynucleotide sequence and are designed on the basis of the predefined target sequence. For example, a first sequencing probe may hybridize to a first target region and a second sequencing probe may hybridize to a second target region. The first and the second target regions may be directly adjacent to each other, may overlap or may be separated by a nucleotide sequence. In preferred embodiments, sequencing probes comprise a number of degenerated bases or universal bases ("n" in FIG. 2) and a single specific nucleotide at probe terminus. Preferably the specific nucleotide is at the 3' terminus. The degenerate sequence allows for the stabilization of the formed duplex, and for the attachment of the label. Practically, a pool of sequencing probes are used, the sequence "nnnnn" being a set of probes having all possible combinations of the A, T, G, C or A, T, U, C nucleotides. In some embodiments, the sequencing probes have a degenerate sequence and a specific single nucleotide at the 3' terminus (nnnnnX, wherein X is A, T (U), G, or C). A set of four different probes may be used to interrogate a specific position of the predefined target sequence, the four probes being identical except at a single position wherein the four different probes have a different terminal base (A, T, G, or C). Yet in other embodiments, the sequencing probes have a degenerate sequence and at least one specific nucleotide at the 3' terminus (nnnnXY, wherein X and Y can represent the same or different nucleotide). According to these embodiments, the sequencing probes allows for sequencing two or more bases at a time. In an exemplary embodiment, the sequencing probes have a degenerate or universal sequence and two specific nucleotides at the 3' (or 5' terminus). A set of sixteen different probes may be used to interrogate a specific position of the predefined target sequence, the sixteen probes being identical except at a specific dinucleotide position wherein the sixteen different probes have a different terminal dinucleotide (AA, TT, GG, CC, AT, AG, AC, TA, TG, TC, CA, CT, CG, GA, GC, GT). In some embodiments, universal bases which hybridize to more than one base may be used. In some embodiments, the sequencing probe is a 6-mer and comprises 5 degenerated bases and one specific nucleotide. In other embodiments, the sequencing probe is a N-mer and comprises (N-1) degenerate bases, N being at least 2 bases long, at least 3 bases long, at least, 4 bases long, at least 5 bases long, at least 10 bases long. In some embodiments, a single RNA position is provided in the deoxyribonucleotide sequencing probe. For example, the terminal interrogating nucleotide is a RNA base rA, rG, rU, or rC.

In some embodiments, four differently labeled sequencing probes are combined to interrogate a single specific position at each discrete feature of the support. For example, referring to FIG. 3, four pools are used, each with a different specific base at its 5' or 3' terminus and with a different label corresponding to the interrogation position. In some embodiments, four pools are used: Red-nnnnnA, Green-nnnnnG, Blue-nnnnnT, and Yellow-nnnnnT, at each discrete feature comprising different target polynucleotide-anchor oligonucleotide hybrids. Yet in other embodiments, the sequencing probe may comprise two or more specific base at its 5' or 3' terminus to allow multiple base sequencing, and speed up the sequencing. In an exemplary embodiments, two bases are sequenced at a time and sixteen different labels may be used to differentiate all the possible nucleotide combinations. One would appreciate that each interrogating cycle allows the interrogation of a plurality of bases and the sequencing process can therefore be achieved in highly parallel fashion. Alternatively, in some embodiments, the reactions are done sequentially, and a same label may be used for each sequencing probe.

In some embodiments, the sequencing probes described herein, may have a wide range of length, varying from 3 to 50 or to 100 bases. In a preferred embodiment, the sequencing probes lengths are in the range of about 5 to about 25, of about 6 to about 20, of about 5 to about 15 bases.

In some embodiments, the sequencing by ligation provides methods in which anchor and sequencing probes are hybridized to directly adjacent regions of the target polynucleotide and are ligated forming a probe ligation product. Preferably, the method further includes a step of removing the unligated probe after the step of ligation. By ligation is meant any method of joining two or more nucleotides to each other. A sequencing probe may be ligated to the anchor oligonucleotide or anchor oligonucleotide subjected to nucleotide extension using conventional procedures, for example, chemical or enzymatic ligation, including DNA ligase I, DNA ligase II, DNA ligase III, DNA ligase IV, E. Coli DNA ligase, T4 DNA ligase, T4 RNA ligase 1, T4 RNA ligase 2, T7 ligase, T3 DNA ligase, thermostable ligase (taq ligase), Tth ligase and the like. The sensitivity of the sequencing process is dependent on the fidelity of the ligase. Preferably, the DNA ligase is a Taq ligase, a Tth ligase, a Pfu ligase or Ampligase. It has been previously shown that DNA ligases can discriminate up to nine bases upstream and downstream of the ligation or junction position (Housby & Southern, NAR, 1998; Pritachrd & Southern, NAR, 1997). One would appreciate that the fidelity of ligation of the DNA ligases such as Tth selectively allows for the incorporation of fully complementary sequencing probes (without base mismatch) and accurate sequencing. The influence of temperature on the specificity of DNA ligases has been shown For example, the thermostable ligase Thermus thermophilus Tth DNA ligase is used at temperature optimized to ensure the specificity of the ligation reaction. In some embodiments, longer oligonucleotides are ligated under conditions such as the ligase is used at temperature above 40° C. Yet in other embodiments, shorter oligonucleotides such as pentamers or nonamers are ligated a temperature of 0° C. thereby decreasing the complexity of the oligonucleotide pool from $4^9$ or 262,144 to $4^5$ or 1024 or a decrease in complexity of 256-fold and a correspondingly stronger signal. Hence, sequencing of the predefined target molecule may involve ligation of sequencing probes which do not necessarily include terminal bases interrogating consecutive positions on the target polynculeotide. For example, the sequencing terminal base of a first sequencing probe interrogates a first interrogation position on the target polynucleotide sequence and the sequencing terminal base of a second sequencing probe interrogates the n interrogation position on the target polynucleotide wherein n is 2, 3, 4, 5, 6, 7, 8, or 9 bases upstream or downstream the first interrogation position.

Figure 3:
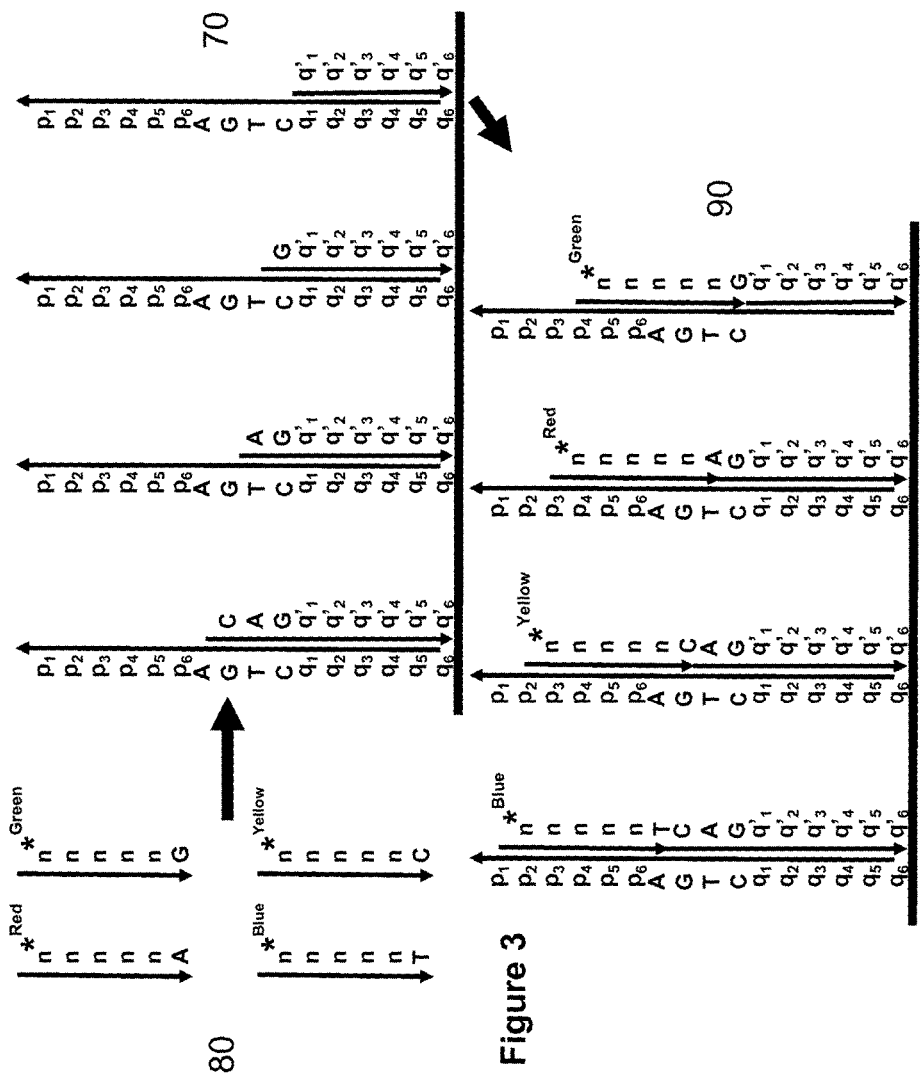
FIG. 3 is a schematic illustration of an embodiment of color ligation probes for use in the ligation based re-sequencing polynucleotide methods.

Methods for sequencing by ligation a target polynucleotide having a predefined sequence are illustrated in FIGS. 1-3 and 7-10. In an exemplary embodiment, and referring to FIG. 1, a heterogeneous population of DNA constructs (10) with primer binding sites is diluted to a single molecule concentration (20) and then amplified in a PCR reaction by means of end primers (30) and (40) in order to create a clonal population (50) of DNA constructs as in known in the art. Referring to FIG. 2, the clonal population of DNA constructs (50) is hybridized to a ligation based re-sequencing oligonucleotide array 60 consisting of a descending stair case of DNA oligonucleotides corresponding to the intended sequence of the DNA construct or target polynucleotide. After hybridization, a surface comprising bound DNA constructs (50) to oligonucleotide array (60) is formed (70). Referring to FIG. 3, single shot re-sequencing by ligation is carried by exposing said surface (70) to a 4 color library of ligation probes (80) consisting of a series of degenerate bases n (which may be about 3 to 9) followed by a single specific base. The probe library (80) is hybridized to the surface (70) and subsequently ligated using enzymatic ligation followed by a wash step. A colorimetric analysis of the DNA array surface is then able to directly determine the base sequence at features or spots on the DNA array thus giving a single shot direct interrogation of whether the DNA construct is the one intended or not (i.e. has the predefined sequence). If one of the bases is incorrect, the ligase which is highly selective will have a lower probability of ligating the ligation probe.

Aspects of the invention relate to a method of sequencing a polynucleotide having a predefined sequence, the method including iterative cycles of ligation to a labeled sequencing probes, detection of the presence or absence of the label and cleavage of the sequencing probes. In some embodiments, the sequencing probe is M nucleotides long and includes (M-1), (M-2), (M-3) . . . degenerated nucleotides and one or more interrogation nucleotides. Each cycle allows for the interrogation of one or more nucleotides and the removal of (M-1), (M-2), (M-3) from the 5' end of the ligated product. According to aspects of the invention, at each cycle, the anchor oligonucleotide is elongated by one, two, three or more nucleotides. In some embodiments, the sequencing probe includes a single RNA base to provide for a site of RNase cleavage. The RNase cleaved the RNA base at its 3' end, thereby leaving the deoxyribonucleotides that are located 3' of the RNA base. In some embodiments, the RNA base is at the 3' terminus of the sequencing probe and after annealing, ligation and detection of the presence or absence of the label, the sequencing oligonucleotide is cleaved and removed using a RNase (referred herein as 0th base cleavage). In other embodiments, the RNA base or ribonucleotide is embedded within the sequencing probe thereby allowing the incorporation of at least one nucleotide at the 5' end of the anchor oligonucleotide. Depending on the position of the RNA base, the anchor oligonucleotide sequence can be extended by a single nucleotide at a time (referred herein as $1^{st}$ base cleavage) or more than one nucleotide at a time (i.e. $x^{th}$ base cleavage wherein x is at least 2). In an other embodiment, oligonucleotides having an acid labile phosphoramidate bond can be used and the ligated oligonucleotides can be cleaved off. Depurination caused by this hydrolysis can be mitigated by using 7-deazapurines. (Shchepinov et al., 2001 Nucleic Acids Res 29, 3864).

Figure 9A:
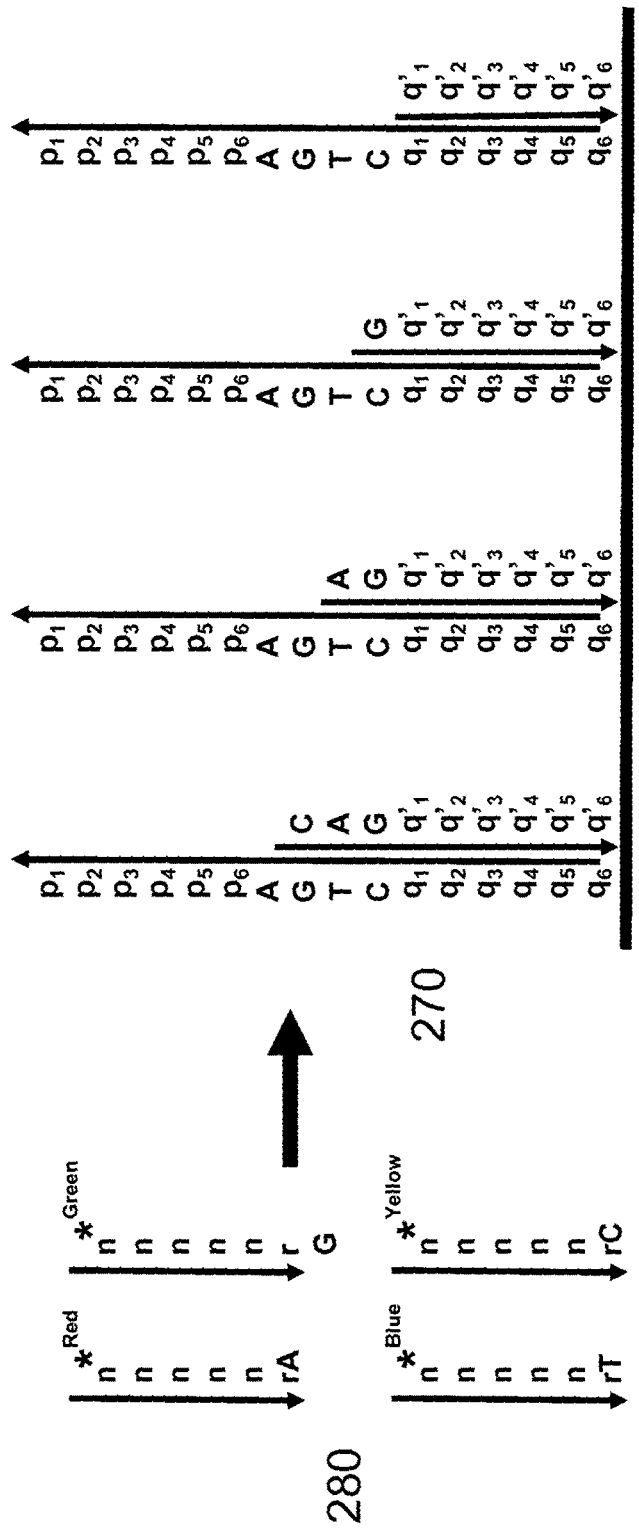
FIG. 9a-c is a schematic illustration of an embodiment of a method of ligation-based re-sequencing oligonucleotide array using a sequencing probe having a ribonucleotide.
Figure 9B:
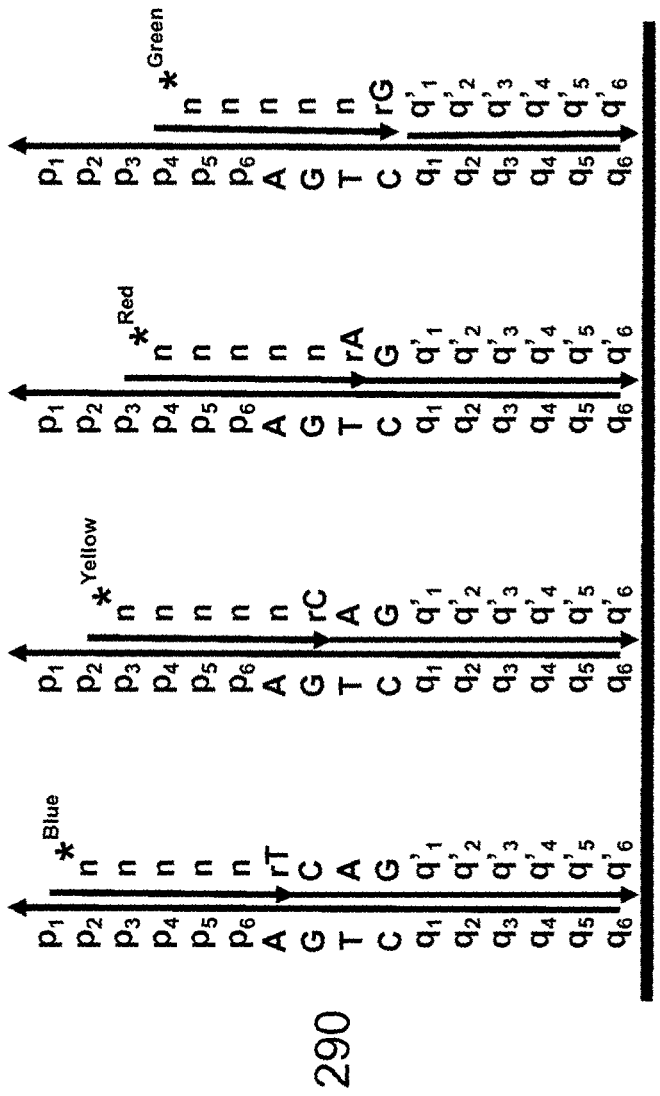
Figure 9C:
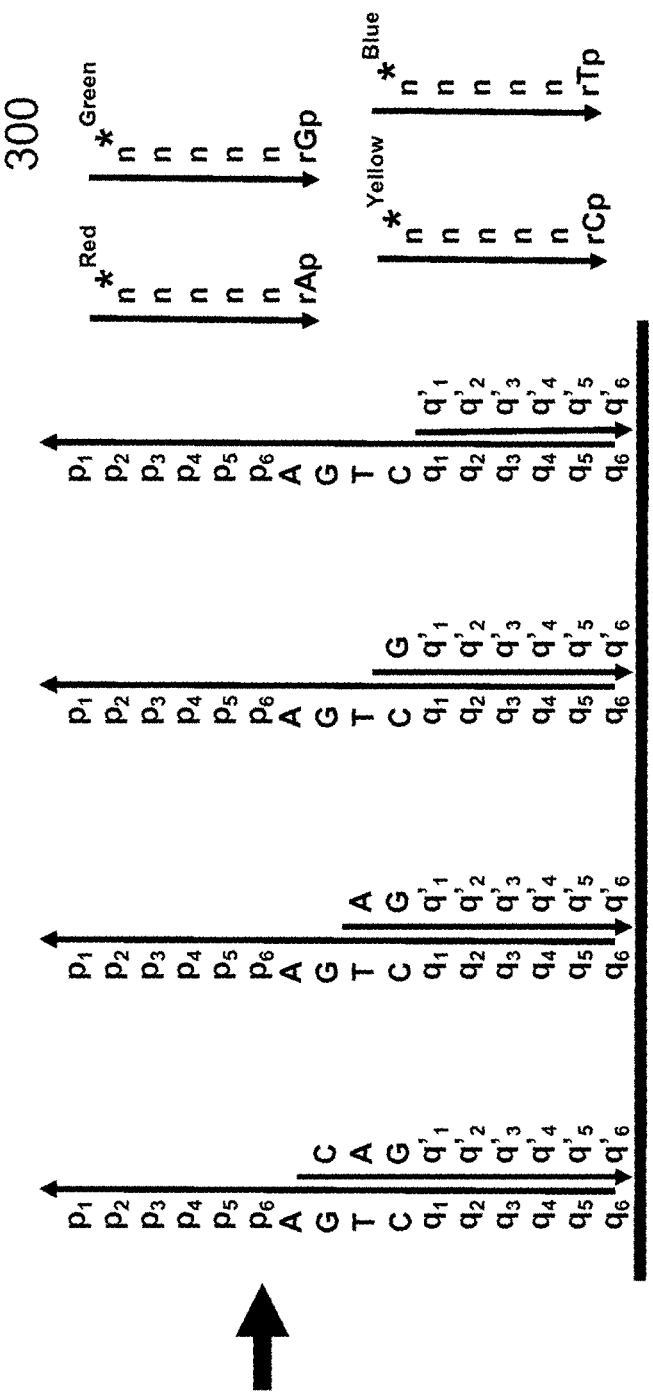

Aspects of the invention relate to a method of sequencing a polynucleotide having a predefined sequence, the method includes ligation to a labeled sequencing probes, detection of the presence or absence of the label and cleavage of the sequencing probes to regenerate the anchor oligonucleotide. An example of this embodiment is illustrated in FIG. 7-10. Referring to FIGS. 7a and 7b, a heterogeneous population of DNA constructs (200) with primer binding sites is diluted to a single molecule concentration (220) (FIG. 7a) and then amplified in a PCR reaction by means of end primers (230) and (240) in order to create a clonal population (250) of DNA constructs (FIG. 7b). Referring to FIG. 8, the clonal population of DNA constructs (250) is hybridized to a ligation based re-sequencing oligonucleotide array (260) consisting of a descending stair case of anchor oligonucleotides corresponding to the intended sequence of the DNA construct. After hybridization a surface comprising polynucleotide sequences (250) hybridized to oligonucleotides (260), a hybridized array (270) is formed. Referring to FIG. 9a-b, single shot re-sequencing by ligation is carried by exposing the surface 270 to a 4 color library of ligation probes (280) consisting of a series of degenerate bases n (which may be about 3 to 9) followed by a single specific RNA base. The probe library (280) is hybridized to the surface (270) and subsequently ligated using enzymatic ligation followed by a wash step. A colorimetric analysis of the DNA array surface is used to directly determine the base sequence at features or spots on the DNA array thus giving a single shot direct interrogation of whether the polynucleotide construct is the one intended or not (i.e. has the predefined sequence). If one of the bases is incorrect, the ligase which is highly selective will have a lower probability of ligating the ligation probe. Referring to FIG. 9c, the array comprising ligated products (290) is subjected to an RNase or RNase H under alkali conditions and then washed. The array, comprising the anchor oligonucleotide probes, is then regenerated and ready for a new round of sequencing of a different clonal population. In some embodiments, the array is regenerated under alkali conditions for example 0.3 M NaOH or KOH at 70° C. for 1.5 h.

Figure 10:
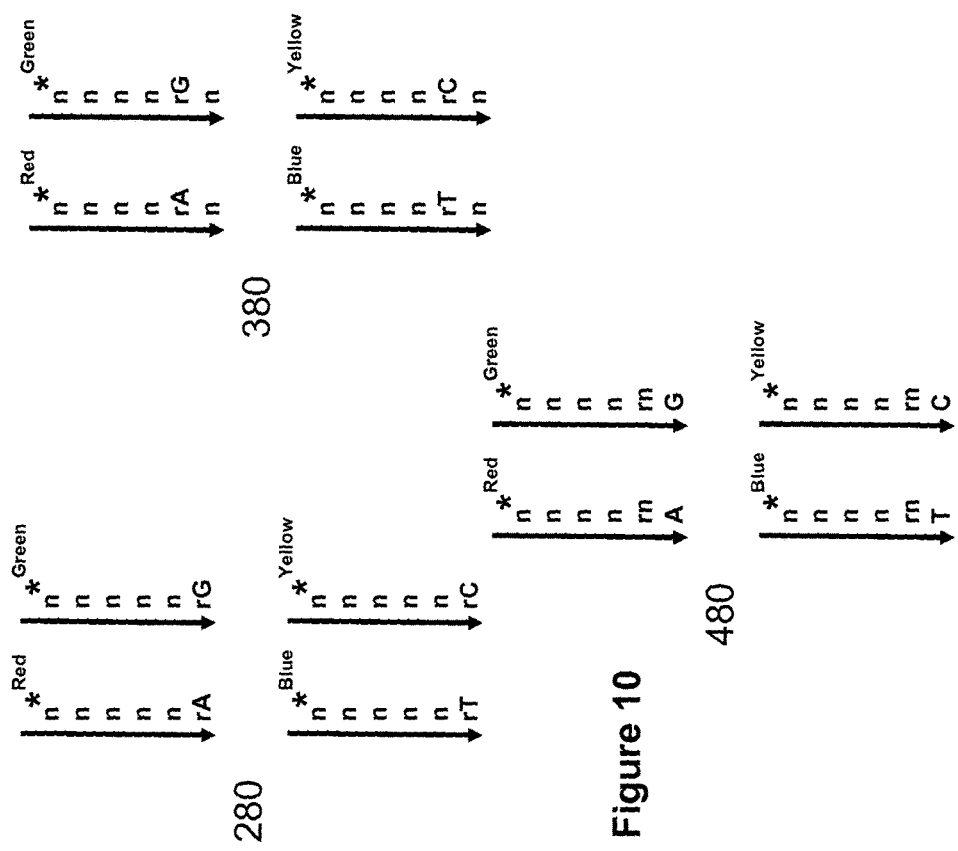
FIG. 10 is a schematic illustration of an embodiment of a method of ligation-based re-sequencing oligonucleotide array using a sequencing probe comprising two ribonucleotides.

In some embodiments, in order to minimize the number of oligonucleotides which must be synthesized on a support, after cleavage of the first sequencing oligonucleotide, a second sequencing oligonucleotide (380), designed as illustrated in FIG. 10, can be used with the non-degenerate position being at (-2) from the ligation joint. FIG. 10 shows degenerate oligonucleotides (480) with the ribonucleotide at the second position from the 3' end enabling the addition of a nucleotide onto the anchor oligonucleotide at each ligation step and thereby moving the ligation position one base in each ligation step.

Sequencing by Polymerase

In some aspect of the invention, the target polynucleotide is sequenced by sequencing by polymerase methods. In some embodiments, the methods of sequencing by polymerase use a combination of anchor probes immobilized on a solid support and labeled nucleotides. In a first step, the target polynucleotide is hybridized to the plurality of anchor oligonucleotides immobilized on discrete features. The resulting hybrid comprising the hybridized target polynucleotide is then contacted with labeled nucleotides in presence of a polymerase. In some embodiments, the methods involve detecting and identifying individual fluorogenic dNTP molecules as a polymerase incorporates them into a single nucleic acid molecule. Suitable nucleobases include, but are not limited to, adenine, guanine, cytosine, uracil, thymine, deazaadenine and deazaguanosine. In a preferred embodiment, each type of base is differently labeled. Each differently labeled base provides a unique detectable signal upon incorporation into the extension product. The polymerase should have a fidelity (incorporation accuracy) of at least 99%. Examples of suitable polymerases include 17 DNA polymerase, T5 DNA polymerase, HIV reverse transcriptase, *E. coli* DNA pol I, T4 DNA polymerase, T7 RNA polymerase, Taq DNA polymerase and *E. coli* RNA polymerase. Exonuclease-defective versions of these polymerases are preferred. After incorporation of the labeled nucleotides, detection of the label is performed to determine if the target polynucleotide has the correct predefined sequence.

Figure 4:
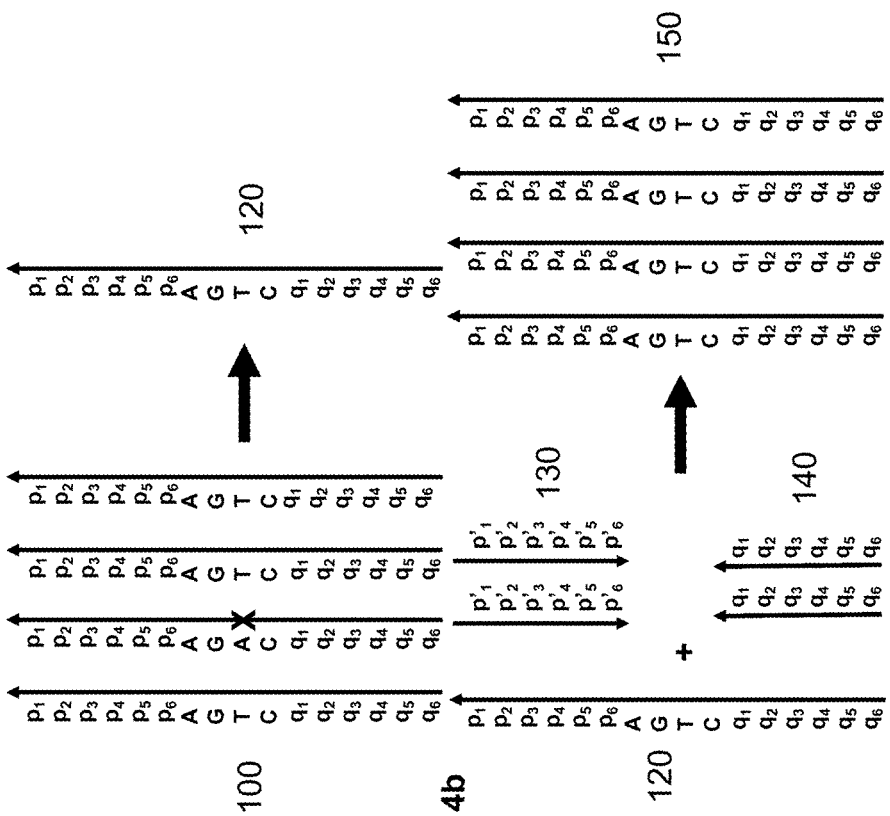
FIGS. 4a and 4b are schematic illustration of an embodiment of a method of preparation of a clonal ensemble of polynucleotide constructs with primer binding sites for use in the polymerase-based re-sequencing methods.
Figure 5:
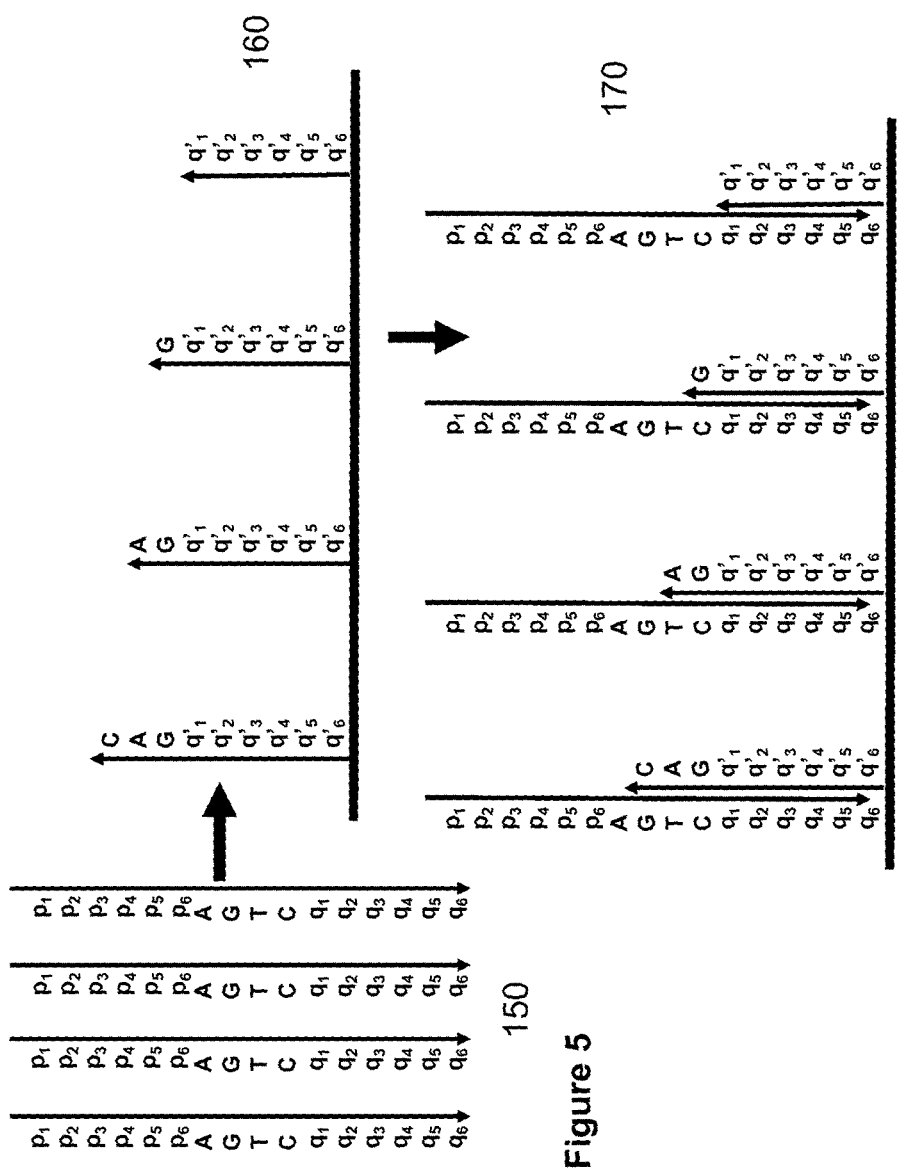
FIG. 5 is a schematic illustration of an embodiment of a method of polymerase-based re-sequencing oligonucleotide array.
Figure 6:
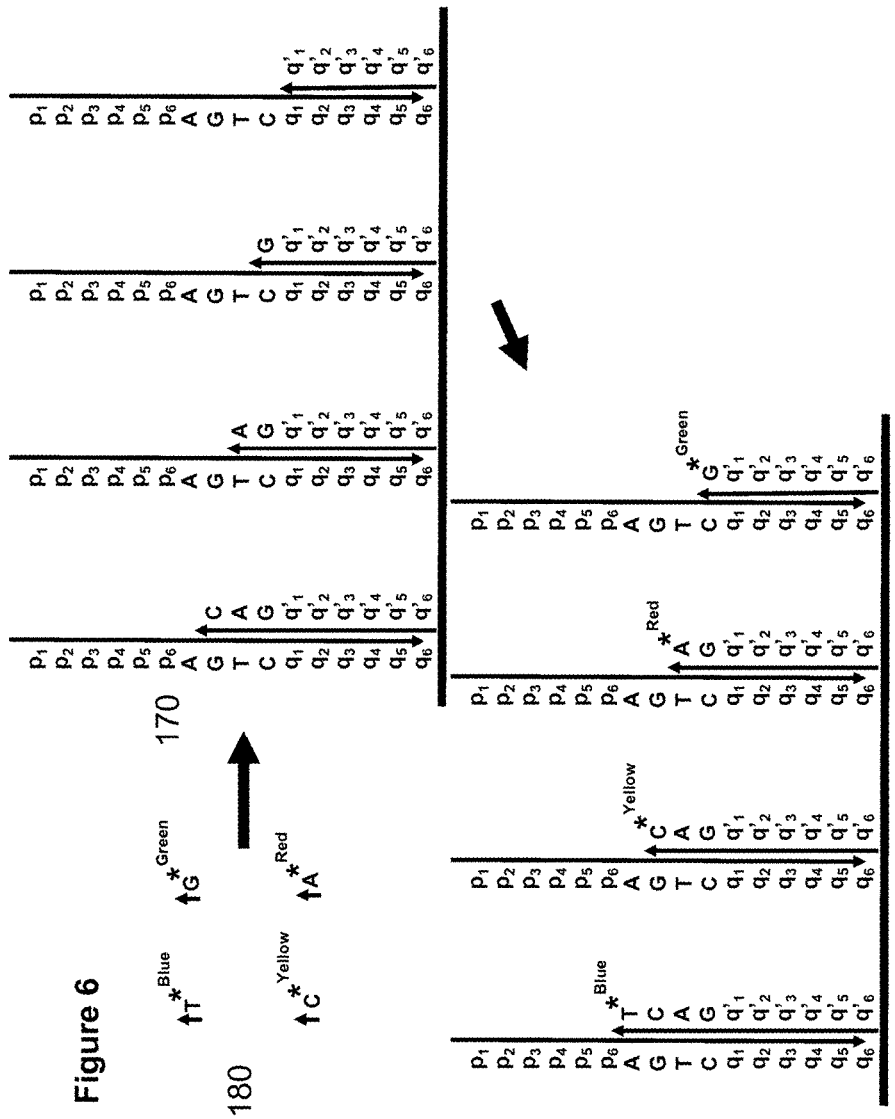
FIG. 6 is a schematic illustration of an embodiment of color nucleotides or use in the polymerase based re-sequencing oligonucleotide array.

Methods for sequencing by polymerase a target polynucleotide having a predefined sequence are illustrated in FIGS. 4-6. Referring to FIGS. 4a and 4b, a heterogeneous population of DNA constructs (100) with primer binding sites is diluted to a single molecule concentration (120) (FIG. 4a) and then amplified in a PCR reaction by means of end primers (130) and (140) in order to create a clonal population (150) of DNA constructs (FIG. 4b) as in known in the art. Referring to FIG. 5, the clonal population of DNA constructs (1500 is hybridized to a polymerase based re-sequencing oligonucleotide array (1600 consisting of a descending stair case of DNA oligonucleotides corresponding to the intended sequence of the DNA construct. After hybridization, a surface comprising bound DNA construct (150) to oligonucleotide array (160) is formed (170). Referring to FIG. 6, single shot re-sequencing by polymerization is carried out by exposing said surface (170) to four fluorescent labeled dNTPs (180). A single labeled dNTP (180) is incorporated into each exposed 3' end on surface (170). A colorimetric analysis of the oligonucleotide array surface is then used to directly determine the base sequence at each spot or feature on the oligonucleotide array thus giving a single shot direct interrogation of whether the DNA construct is the one intended or not (i.e. has the predefined sequence).

In some embodiments, the method of sequencing a polynucleotide having a predefined sequence includes iterative cycles of extension and detection of the presence or absence of the label. Iterative cycles allow for the polymerase to sequentially extend the anchor oligonucleotide by incorporating labeled nucleotides which are complementary to the target polynucleotide sequence. In some embodiments, positive hybridization outcome are used to deduce target polynucleotides having the correct sequence and negative hybridization outcomes are used to eliminate the polynucleotide having the incorrect sequence or having a mismatch.

Devices and methods to selectively isolate the correct nucleic acid sequence from the incorrect nucleic acid sequences are provided herein. The correct sequence may be isolated by selectively isolating the correct sequence from the other incorrect sequences as by selectively moving or transferring the desired assembled polynucleotide having a predefined sequence to a different feature of the support. Alternatively, polynucleotides having an incorrect sequence can be selectively removed. According to some methods of the invention, the assembly product target polynucleotide may first be diluted onto the solid support in order to obtain a clonal population of target polynucleotides (i.e a population containing a single target polynucleotide sequence). As used herein, a "clonal nucleic acids" or "clonal population" or "clonal polynucleotide" are used interchangeably and refer to a clonal molecular population of nucleic acids, i.e. to nucleic acids or polynucleotide that are substantially or completely identical to each other. Accordingly, the dilution based protocol provides a population of nucleic acids or polynucleotide being substantially identical or identical to each other. In preferred embodiments, the polynucleotides are diluted serially. In some embodiments, the device or array integrates a serial dilution function. In some embodiments, the assembly product is serially diluted to a produce a clonal population of nucleic acids. Preferably, the concentration and the number of molecules is assessed prior to the dilution step and a dilution ratio is calculated in order to produce a clonal population. In an exemplary embodiment, the assembly product is diluted by a factor of at least 2, at least 3, at least 4, at least 5, at least 6, at least 7, at least 10, at least 20, at least 50, at least 100, at least 1,000 etc.

In preferred embodiments, the target polynucleotides are amplified after obtaining clonal populations. In some embodiments, the target polynucleotide may comprise universal (common to all oligonucleotides), semi-universal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, a target polynucleotide contains both universal and unique amplification sequences, which can optionally be used sequentially.

In some embodiments, primers/primer binding site may be designed to be temporary. For example, temporary primers may be removed by chemical, light based or enzymatic cleavage. For example, primers/primer binding sites may be designed to include a restriction endonuclease cleavage site. In an exemplary embodiment, a primer/primer binding site contains a binding and/or cleavage site for a type IIs restriction endonuclease. In such case, amplification sequences may be designed so that once a desired set of oligonucleotides is amplified to a sufficient amount, it can then be cleaved by the use of an appropriate type IIs restriction enzyme that recognizes an internal type IIs restriction enzyme sequence of the oligonucleotide. In some embodiments, after amplification, the pool of nucleic acids may be contacted with one or more endonucleases to produce double-stranded breaks thereby removing the primers/primer binding sites. In certain embodiments, the forward and reverse primers may be removed by the same or different restriction endonucleases. Any type of restriction endonuclease may be used to remove the primers/primer binding sites from nucleic acid sequences. A wide variety of restriction endonucleases having specific binding and/or cleavage sites are commercially available, for example, from New England Biolabs (Beverly, Mass.).

In certain exemplary embodiments, a detectable label can be used to detect one or more nucleotides and/or oligonucleotides described herein. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorimidases, phosphatases, peroxidases, cholinesterases and the like. Identifiable markers also include radioactive compounds such as 125I, 35S, 14C, or 3H. Identifiable markers are commercially available from a variety of sources. Preferably the oligonucleotide probes or nucleotides are fluorescently labeled with four different fluorophores, each fluorophore being associated to a particular base or nucleotide.

Described below are methods for sequencing by ligation a target polynucleotide having a predefined sequence. In an exemplary embodiment, and referring to FIG. 1, a heterogeneous population of DNA constructs (10) with primer binding sites is diluted to a single molecule concentration (20) and then amplified in a PCR reaction by means of end primers (30) and (40) in order to create a clonal population (500 of DNA constructs as in known in the art. Referring to FIG. 2, the clonal population of DNA constructs 50 is hybridized to a ligation based re-sequencing oligonucleotide array (60) consisting of a descending stair case of DNA oligonucleotides corresponding to the intended sequence of the DNA construct. After hybridization a surface comprising bound DNA constructs (50) to oligonucleotide array (60) is formed (70). Referring to FIG. 3, single shot re-sequencing by ligation is carried by exposing said surface (70) to a four color library of ligation probes (80) consisting of a series of degenerate bases n (which may be about 3 to 9) followed by a single specific base. The probe library (800 is hybridized to the surface (70) and subsequently ligated using enzymatic ligation followed by a wash step. A colorimetric analysis of the DNA array surface is then used to directly determine the base sequence at features or spots on the DNA array thus giving a single shot direct interrogation of whether the DNA construct is the one intended or not (i.e. has the predefined sequence). If one of the bases is incorrect, the ligase which is highly selective will have a lower probability of ligating the ligation probe.

In another exemplary embodiment and referring to FIG. 4, a heterogeneous population of DNA constructs (1000 with primer binding sites is diluted to a single molecule concentration (120) and then amplified in a PCR reaction by means of end primers (130) and (140) in order to create a clonal population (150) of DNA constructs as in known in the art. Referring to FIG. 5, the clonal population of DNA constructs (150) is hybridized to a polymerase based re-sequencing oligonucleotide array (160) consisting of a descending stair case of DNA oligonucleotides corresponding to the intended sequence of the DNA construct. After hybridization a surface comprising bound DNA construct (150) to oligonucleotide array (160) is formed (170). Referring to FIG. 6, single shot re-sequencing by polymerization is carried out by exposing said surface (170) to four fluorescent labeled dNTPs (180). A single labeled dNTP (180) is incorporated into each exposed 3' end on surface (170). A colorimetric analysis of the oligonucleotide array surface is then used to directly determine the base sequence at each spot or feature of the oligonucleotide array thus giving a single shot direct interrogation of whether the DNA construct is the one intended or not.

Aspects of the invention relate to the facilitation of accurate synthesis of nucleic acids. In some embodiments, the target polynucleotide sequence is synthesized de novo (such as by ligation or by chain extension). In some embodiments, sequence information is obtained by sequencing by ligation or sequencing by polymerase as described above. Site directed mutagenesis may be used to correct at least one error in the synthesized nucleotide sequence.

Aspects of the invention relate to the read out to identify synthetic oligonucleotide or nucleic acid having the correct sequences (e.g. predefined sequences). One skilled in the art would appreciate that, during oligonucleotide synthesis, random base errors may be introduced. In some embodiments, correct nucleic acid sequences synthesized using methods known in the art can be identified according to the identification methods disclosed herein. For example, the methods disclosed herein can be used to identify high fidelity nucleic acid sequences prior to oligonucleotide assembly. Accordingly, aspect of the invention relate to the identification of correct oligonucleotide sequences to produce synthetic custom polynucleotides having lower error rates than synthetic polynucleotides made by the methods known in the art. In some embodiments, high fidelity synthetic oligonucleotides can be identified, by first diluting the synthetic oligonucleotides to obtain a clonal population of oligonucleotides (i.e., a population containing a single oligonucleotide sequence). As used herein, a "clonal nucleic acids" or "clonal population" or "clonal oligonucleotides" are used interchangeably and refer to a molecular population of nucleic acids that are substantially or completely identical to each other; including without limitation, a population of nucleic acids that are synthesized from a single template nucleic acid, or are amplification products of an amplification process starting with a single template. Accordingly, the dilution based protocol provides a population of nucleic acids or oligonucleotides (or polynucleotides) being substantially identical or identical to each other. In some embodiments, the oligonucleotides are diluted serially. In some embodiments, the oligonucleotides are diluted in solution or onto a solid support. In some embodiments, the synthetic oligonucleotides or nucleic acids are serially diluted to a produce a clonal population of nucleic acids. The concentration and the number of molecules can be assessed prior to the dilution step and a dilution ratio is calculated in order to produce a clonal population. In an exemplary embodiment, the synthetic oligonucleotides or nucleic acids are diluted serially by a factor of at least 2, at least 3, at least 4, at least 5, at least 6, at least 7, at least 10, at least 20, at least 50, at least 100, at least 1,000, etc to a final dilution of about $1/1000$, $1/10,000$, $1/100,000$, $1/1,000,000$ to obtain a clonal population of oligonucleotides or nucleic acids. In some embodiments, the oligonucleotide or nucleic acid sequences are amplified in solution or on a support. The amplified oligonucleotide or nucleic acid sequences can be divided into pools for subsequent sequence verification. The sequence of the clonal population of oligonucleotides can then be identified according to the methods disclosed herein. In further preparations or processes, the methods, compositions, and/or devices described herein can be used as a quality control measure or an error control process. For example, in the assembly of oligonucleotides to form a desired polynucleotide, the oligonucleotides may be sequence verified at any point during the assembly process by producing clonal populations of oligonucleotides, verifying the sequence of the populations (or a subset of populations) with an aliquot of the oligonucleotides from each population, and using some or all of the remaining oligonucleotides from a sequence-verified population for further assembly.

Aspects of the methods and devices provided herein may include automating one or more acts described herein. In some embodiments, one or more steps of an amplification and/or sequencing reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

The microarray substrate was prehybridized with 1.2 ml of 10 mM Tris-HCl pH 7.4, 5 mM $MgCl_2$, 200 µg/ml BSA (bovine serum albumin) for 30 minutes at 37° C. The microarray was then treated with T4 polynucleotide kinase (PNK, Enzymatics) at a concentration of 200 U/ml (0.2 U/µl) for 30 minutes at 37° C. in T4 ligase buffer (Enzymatics) with the addition of 0.005% Triton X-100. The chip was washed with 1×SSPE containing 0.005% Triton X-100 (SSPET) and kinase was inactivated at 65° C. for 20 minutes. Template was hybridized in SSPET at a concentration of 40 nM (2.5 µg/ml of 200-mer) for 3-18 hours at 56° C. and washed 2 times with SSPET at 56° C. Hybridization is detected by ligating fluorescent nonamers with T4 DNA ligase at a concentration of 2400 U/ml at 32° C. for 30 minutes. The microarray was then washed 3 times with 0.1×SSPE at 97° C. and rinsed once with water. The microarray was scanned at 543 nm for Cy3 detection, at 594 nm for Texas Red detection, at 633 nm for Cy5 detection and at 488 nm for FAM.

In a first example, a colorimetric analysis of the microarray after hybridization of a wild-type sequence (e.g. predefined sequence) and a variant sequence having three substitutions was performed. The colorimetric assay of the wild-type sequence showed the Ts as green, Gs as blue, Cs as red and As as blank. The colorimetric assay of the variant sequence confirmed the following substitutions: A209 was substituted to a T, C249 was substituted to T, and T333 was substituted to G. The substitutions resulted in a green spot (T) appearing in the blank field (A), a green spot (T) appearing in the red field (C) and a blue spot (G) in the green field (T).

In a second example, a colorimetric analysis of a microarray after hybridization of a wild-type sequence (e.g. predefined sequence) and a variant sequence. The variant sequence harbored an insertion (C) at position 14 of the wild type sequence.

```
                                           (SEQ. ID. No. 1)
    Wild type: GGTGGATGAAGCCATCGCGGCGTGTGG
                                           (SEQ. ID. No. 2)
    Variant:   GGTGGATGAAGCCCATCGCGGCGTGTGG
```

The colorimetric assay of the wild-type sequence showed Ts as red, Gs as green, Cs as blue and As as blank. This resulted in a blank spot (no ligation reaction has occurred as the result of the mismatch) in the green field (G), green spot (G) appearing in the red field (T), and a red spot (T) appearing in the blank field (A).

INCORPORATION BY REFERENCE

Reference is made to U.S. Pat. No. 7,276,338, U.S. Pat. No. 7,604,941, U.S. Patent Application 20060008833, U.S. Patent Application 20100063264, to U.S. provisional application 61/334,426 entitled "METHODS FOR NUCLEOTIDE SEQUENCING AND HIGH FIDELITY POLYNUCLEOTIDE SYNTHESIS", filed May 13, 2010, to U.S. provisional application 61/347,207 entitled "METHODS FOR NUCLEOTIDE SEQUENCING AND HIGH FIDELITY POLYNUCLEOTIDE SYNTHESIS", filed May 21, 2010, to U.S. provisional application 61/363,066 entitled "METHODS FOR NUCLEOTIDE SEQUENCING AND HIGH FIDELITY POLYNUCLEOTIDE SYNTHESIS", filed Jul. 9, 2010. All publications, patents mentioned herein are hereby incorporated by reference in their entirety as if each individual patent or publication was specifically and individually indicated to be incorporated by reference.

The invention claimed is:

1. A method for interrogating at least one nucleotide position of a target polynucleotide, the method comprising:
   a. providing a support comprising a plurality of anchor oligonucleotides immobilized thereon, wherein each anchor oligonucleotide comprises a terminal region complementary to a first region of a target polynucleotide, wherein at least two anchor oligonucleotides differ in length from one another by one or more predefined nucleotide, and wherein the plurality of anchor oligonucleotides together comprise a predefined portion of the target polynucleotide to be determined;
   b. hybridizing the target polynucleotide to a first anchor oligonucleotide at the first region of the target polynucleotide;
   c. contacting the target polynucleotide, hybridized to the first anchor oligonucleotide, with a sequencing oligonucleotide probe, wherein the sequencing oligonucleotide probe comprises an interrogating nucleotide at the 3' and/or 5' terminus, a label, and a portion complementary to a second region of the target polynucleotide; wherein the sequencing oligonucleotide probe is provided in a pool comprising at least four differently labeled sequencing probes each having a different interrogating nucleotide;
   d. ligating the sequencing oligonucleotide probe with the first anchor oligonucleotide when the interrogating nucleotide forms a base pair with the target polynucleotide at a first interrogated position located between the first region and the second region of the target polynucleotide; and
   e. detecting the presence of the label in the ligation product of step (d) thereby identifying the presence of a corresponding nucleotide at the first interrogated position on the target polynucleotide, the corresponding nucleotide being complementary to the interrogating nucleotide on the sequencing oligonucleotide probe.

2. The method of claim 1 wherein in step (a), the support comprises a plurality of features, each feature having a plurality of anchor oligonucleotides immobilized thereon that differ in nucleotide sequence from another feature.

3. The method of claim 1 wherein the sequencing oligonucleotide comprises at least three degenerate bases.

4. The method of claim 1 wherein the sequencing oligonucleotide comprises at least three degenerate bases and two or more interrogating nucleotides.

5. The method of claim 1 wherein the interrogating nucleotide is at the 3' terminus of the sequencing oligonucleotide probe.

6. The method of claim 1 wherein the label comprises a fluorescence tag.

7. The method of claim 1 wherein the first anchor oligonucleotide comprises at least three degenerate bases.

8. The method of claim 1 further comprising repeating steps c), d) and e) using a second sequencing oligonucleotide probe to identify a second interrogated position.

9. The method of claim 1 wherein the target polynucleotide comprises a first primer binding site at its 5' end and a second primer binding site at its 3' end.

10. The method of claim 1 further comprising, before step b), amplifying the target polynucleotide.

11. The method of claim 1 comprising, in step c), contacting the target polynucleotide with four sequencing oligonucleotide probes, wherein each oligonucleotide probe comprises a unique nucleotide and a different label.

12. The method of claim 1 wherein the ligating step comprises using Tth DNA ligase under condition promoting selective ligation.

13. The method of claim 1 further comprising removing unligated sequencing oligonucleotide probe after the step of ligating.

14. The method of claim 1 wherein the first anchor oligonucleotide is a single-stranded oligonucleotide.

15. The method of claim 1 wherein the first anchor oligonucleotide has at least 5 nucleotides.

16. The method of claim 1 wherein each different anchor oligonucleotide is at least partially complementary to the target polynucleotide.

17. The method of claim 16 wherein each different anchor oligonucleotide comprises bases selected from the group consisting of (i) one or more bases complementary to the target polynucleotide and two or more degenerate bases, (ii) one or more bases complementary to the target polynucleotide and two or more universal bases, and (iii) one or more bases complementary to the target polynucleotide, two or more degenerate bases and two or more universal bases.

18. The method of claim 1 wherein each different anchor oligonucleotide has a common n-mer core.

19. The method of claim 1 wherein each different anchor oligonucleotide differs from one another by a different terminal base.

20. The method of claim 1 wherein each different anchor oligonucleotide differs from one another such that in totality they comprise complementarity to the predefined sequence of the target polynucleotide.

21. The method of claim 2 wherein the plurality of anchor oligonucleotides are immobilized on the support at their 3' end.

22. The method of claim 2 wherein the plurality of anchor oligonucleotides are immobilized on the support via a linker.

23. The method of claim 2 wherein the plurality of anchor oligonucleotides are immobilized on the support via a cleavable linker.

* * * * *

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Synthetic construct

<400> SEQUENCE: 1
ggtggatgaa gccatcgcgg cgtgtgg                                          27

<210> SEQ ID NO 2
<211> LENGTH: 28
<212> TYPE: DNA
<213> ORGANISM: Artificial Sequence
<220> FEATURE:
<223> OTHER INFORMATION: Synthetic construct

<400> SEQUENCE: 2
ggtggatgaa gcccatcgcg gcgtgtgg                                         28
```